United States Patent [19]
Thorson et al.

[11] Patent Number: 6,131,579
[45] Date of Patent: Oct. 17, 2000

[54] WIRE BASED TEMPERATURE SENSING ELECTRODE

[75] Inventors: Ted S. Thorson, Pleasanton; James A. Filice, Sunnyvale, both of Calif.

[73] Assignee: Somnus Medical Technologies, Inc., Sunnyvale, Calif.

[21] Appl. No.: 09/064,023

[22] Filed: Apr. 21, 1998

[51] Int. Cl.⁷ .................................................. A61B 19/00
[52] U.S. Cl. ............................ 128/898; 600/549; 606/1; 606/42
[58] Field of Search ..................... 606/1, 27–34, 606/41, 42; 607/101, 102; 600/549, 374

[56] References Cited

U.S. PATENT DOCUMENTS

| | | | |
|---|---|---|---|
| 4,776,334 | 10/1988 | Prionas | 606/42 |
| 5,071,406 | 12/1991 | Jang | 604/96 |
| 5,087,256 | 2/1992 | Taylor et al. | 606/28 |
| 5,114,423 | 5/1992 | Kasprzyk et al. | 606/27 |
| 5,370,675 | 12/1994 | Edwards et al. | 607/101 |
| 5,529,067 | 6/1996 | Larsen et al. | 600/374 |

*Primary Examiner*—Michael Peffley
*Attorney, Agent, or Firm*—Wilson Sonsini Goodrich & Rosati

[57] ABSTRACT

Systems and methods are described for a wire based temperature sensing electrode for surgical procedures. A temperature sensing energy delivery device includes an elongated member having a groove formed in at least portion of the elongated member; and a first temperature sensor mechanically connected to the elongated member, the first temperature sensor including a first temperature sensor lead that is routed along the groove. The systems and methods provide advantages in that the wire based temperature sensing electrode for surgical procedures can simultaneously accommodate a temperature sensor and associated leads, exhibit sufficient strength without bulk, and be provided at lower cost.

1 Claim, 4 Drawing Sheets

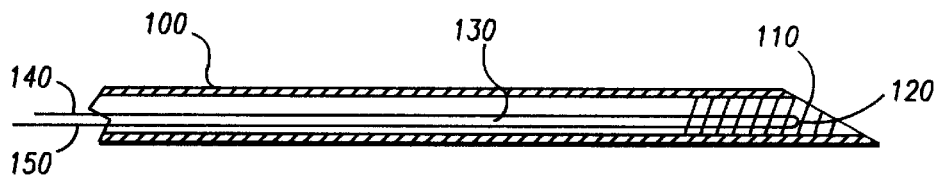
(PRIOR ART)
FIG.−1
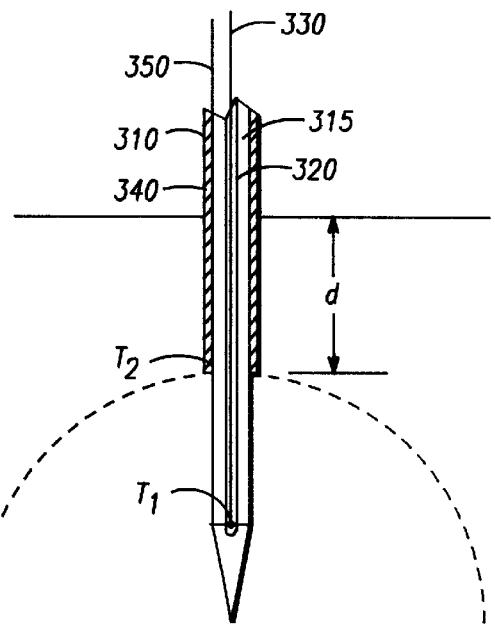
FIG.−3
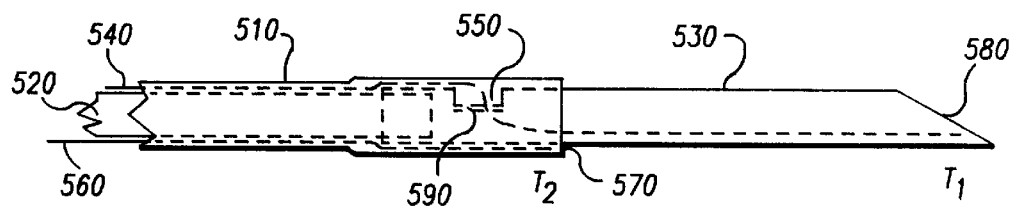
FIG.−5

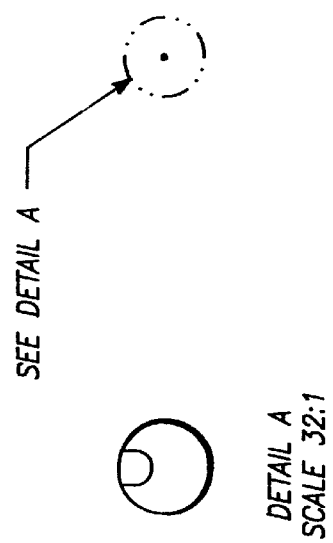
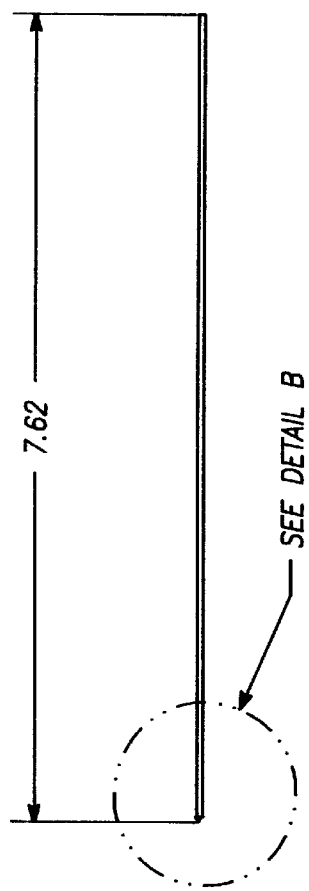
FIG.-7A   FIG.-7D   FIG.-7C   FIG.-7B

WIRE BASED TEMPERATURE SENSING ELECTRODE

BACKGROUND OF THE INVENTION

1. Field of the Invention

The invention relates generally to the field of electrodes for medical treatment. More particularly, the invention relates to a wire based electrode that is provided with a temperature sensing capability without necessarily needing to use any hollow tubing to accommodate the corresponding temperature sensor lead.

2. Discussion of the Related Art

Prior art temperature sensing electrodes, sometimes called temperature sensing energy delivery devices, are known to those skilled in the art. For example, a conventional temperature sensing electrode is typically constructed by threading a thermocouple cable through the central axis of a hollow tube and fixing the junction of the thermocouple to a sharpened tip at a distal end of the hollow tube.

Referring to FIG. 1, a conventional temperature sensing electrode is shown. A stainless steel tube 100 is provided with a sharpened tip 110. The junction 120 of a thermocouple 130 is attached to the interior of the stainless steel tube 100 with an adhesive 140. The thermocouple 130 includes a first wire 140 of a first metal material and a second wire 150 of a second metal material.

A problem with this temperature sensing electrode technology has been that using a hollow tube to accommodate the thermocouple cable reduces the strength of the electrode, compared to a non-temperature sensing, solid wire electrode of equal outer diameter. In the past, in order to address this reduction in strength, the size (i.e., inner and outer diameter) of the hollow tubing was increased to achieve the necessary mechanical strength. However, this scaling-up approach has the twin drawbacks of creating a larger surgical instrument that is more difficult for the surgeon to manipulate and an instrument which cuts a larger hole when inserted into tissue, thereby increasing the invasiveness of a given surgical procedure. Therefore, what is required is a solution that provides a temperature sensing capability in an electrode without increasing the bulk of the electrode.

Another problem with this temperature sensing electrode technology has been that the available hollow tubing that is suitable for surgical insertion into tissue (i.e., tubing having suitable mechanical and corrosion properties) is expensive. In the past, the high cost of hollow tubing based electrodes has simply been endured, thereby inhibiting the wider deployment of temperature sensing electrodes within the surgical community. Therefore, what is also required is a solution that allows the fabrication of a temperature sensing electrodes at lower cost, preferably a much lower cost.

Heretofore, the requirements of accommodating a temperature sensor and the corresponding temperature sensor lead, providing sufficient strength without bulk, and lower cost referred to above have not been fully met with regard to temperature sensing electrodes. What is needed is a solution that simultaneously addresses all of these requirements.

SUMMARY OF THE INVENTION

A primary object of the invention is to provide a wire based temperature sensing electrode. Another primary object of the invention is to provide a method of using a wire based temperature sensing electrode. Another primary object of the invention is to provide a method of making a wire based temperature sensing electrode. Another primary object of the invention is to provide a wire based temperature sensing electrode made in accordance with the method.

In accordance with these objects, there is a particular need for a wire based temperature sensing electrode that includes a temperature sensor whose lead is routed along a groove that is formed in the side of a wire, the wire of the electrode being insertable into the tissue of a patient in need thereof. Thus, it is rendered possible to simultaneously satisfy the above-discussed requirements of i) accommodating a temperature sensor and the corresponding lead of the temperature sensor, ii) sufficient strength without bulk, and iii) low cost, which, in the case of the prior art, are mutually contradicting and cannot be simultaneously satisfied.

A first aspect of the invention is implemented in an embodiment that is based on a temperature sensing energy delivery device, comprising: an elongated member having a groove formed in at least portion thereof; and a first temperature sensor mechanically connected to said elongated member, said first temperature sensor including a first temperature sensor lead that is routed along said groove.

A second aspect of the invention is implemented in an embodiment that is based on a temperature sensing energy delivery device, comprising: an elongated member; a tube substantially coaxially connected to a distal end of said elongated member, said tube including a temperature sensor lead slot; and a first temperature sensor located within said tube, said first temperature sensor having a temperature sensor lead that is routed through said temperature sensor lead slot.

A third aspect of the invention is implemented in an embodiment that is based on a method of using a temperature sensing energy delivery device, comprising: providing the temperature sensing energy delivery device; inserting the temperature sensing energy delivery device into a patient in need thereof; and delivering energy to the patient through the energy delivery device.

A fourth aspect of the invention is implemented in an embodiment that is based on a method of making a temperature sensing energy delivery device, comprising: mounting a distal end of an elongated member so that a portion of a length defined by said elongated member is held substantially rigid; bending a proximal end of said elongated member away from a principle axis defined by the distal end of said elongated member when said elongated member is not bent; and cutting a groove with an electrostatic discharge machining wire.

These, and other, objects and aspects of the invention will be better appreciated and understood when considered in conjunction with the following description and the accompanying drawings. It should be understood, however, that the following description, while indicating preferred embodiments of the invention and numerous specific details thereof, is given by way of illustration and not of limitation. Many changes and modifications may be made within the scope of the invention without departing from the spirit thereof, and the invention includes all such modifications.

BRIEF DESCRIPTION OF THE DRAWINGS

A clear conception of the advantages and features constituting the invention, and of the components and operation of model systems provided with the invention, will become more readily apparent by referring to the exemplary, and therefore nonlimiting, embodiments illustrated in the drawings accompanying and forming a part of this specification, wherein like reference characters (if they occur in more than one view) designate the same parts. It should be noted that the features illustrated in the drawings are not necessarily drawn to scale.

FIG. 1 illustrates a schematic view of a conventional temperature sensing electrode, appropriately labeled "prior art."

FIG. 3 illustrates a schematic view of a wire based temperature sensing electrode inserted into tissue, representing an embodiment of the invention.

FIG. 5 illustrates a schematic view of a wire based temperature sensing electrode, representing an embodiment of the invention.

FIGS. 7A–7D illustrate schematic views of a needle that has undergone wire electrostatic discharge machining, representing an embodiment of the invention.

DESCRIPTION OF PREFERRED EMBODIMENTS

Figure 2A:
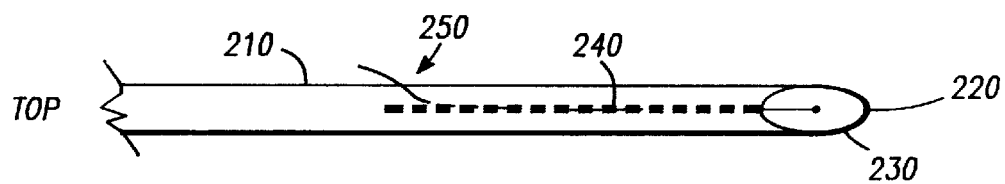
FIGS. 2A–2B illustrate schematic views of a wire based temperature sensing electrode, representing an embodiment of the invention.

The invention and the various features and advantageous details thereof are explained more fully with reference to the nonlimiting embodiments that are illustrated in the accompanying drawings and detailed in the following description. Descriptions of well known components and processing techniques are omitted so as not to unnecessarily obscure the invention in detail.

The context of the invention is surgical procedures with energy delivery devices (e.g., electrodes), particularly radio frequency (RF) powered electrodes. The invention can also be utilized in conjunction with data processing methods that transform the electrode power waveform signals (e.g., RF) that are coupled to the electrode so as to provide power control, as well at to actuate additional interconnected discrete hardware elements, such as, for example, auxiliary electrodes and/or fluid handling devices.

Referring to the drawings, a detailed description of preferred embodiments of the invention is provided with respect to FIGS. 2A through 7D. These drawings depict various aspects of an electrode structure for accommodating at least one temperature sensor and associated leads. The electrode structure must be capable of both accommodating the sensor(s) and conveying the leads to the location on the electrode at which the temperature sensor(s) is(are) to be located.

Figure 2B:
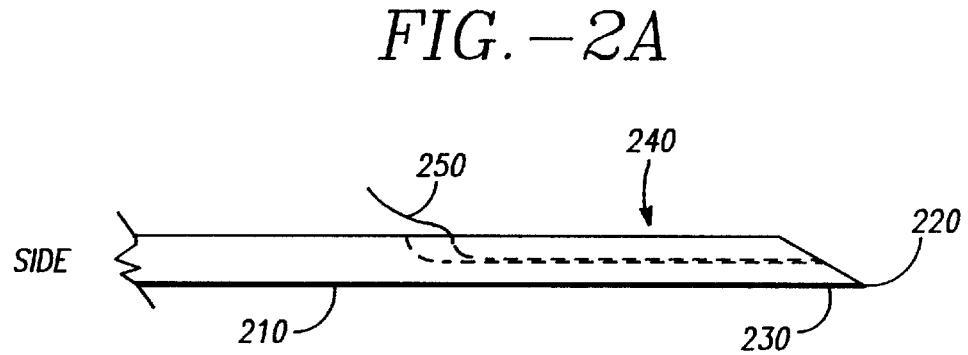

Referring now to FIGS. 2A–2B, a nickel-titanium wire 210 includes a sharp tip 220 at a distal end 230. The nickel-titanium wire 210 represents a generic class of elongated members and is provided with a groove 240. A thermocouple 250 is routed through the groove 240. The thermocouple 250 represents a generic class of temperature sensors. The thermocouple 250 can be a copper-constantan thermocouple. The thermocouple 250 includes a sensor lead that is routed along the groove 240. The thermocouple 250 is held in place with an adhesive, such as, for example, an epoxy. The adhesive physically connects the sensor lead to the groove 240 and fills a portion of the conduit defined by the groove 240 that is not occupied by said first temperature sensor. The thermocouple 250 includes a sensing tip that is mechanically connected to the groove 240 at a position that is located substantially at a distal end of the wire 210. The combined assembly can compose a surgical instrument for delivering energy to a life form. (It should be noted that the surface of a tissue is represented in FIGS. 2A–2B with a wavy line for improved clarity.) Although the preferred embodiment shown in FIG. 1 includes a single thermocouple, it is within the level of ordinary skill in the art after having knowledge of the invention disclosed herein to add additional grooves and/or thermocouples.

It can be seen from FIGS. 2A–2B that the effect of routing the thermocouple 250 through the groove 240 is to maintain the circular outer shape of the wire 210 at its distal end. However, the cross-sectional continuity, and rotational symmetry of metal is disrupted due to the presence of the groove 240.

When the depth of the groove is excessively low, the epoxy, and even the thermocouple wires, may protrude above the surface of the wire. On the other hand, when the depth of the groove is excessively high, the mechanical integrity and/or RF performance of the wire may be compromised.

When the width of the groove is excessively low, the epoxy may not flow in the groove, and the thermocouple wires may not fit in the groove. On the other hand, when the width of the groove is excessively high, the mechanical integrity and/or RF performance of the wire may be compromised.

The particular manufacturing process used for forming the groove 240 should be inexpensive and reproducible. Conveniently, the groove 240 can be formed using any metal cutting method. It is preferred that the process be electrostatic discharge machining. For the manufacturing operation, it is moreover an advantage to employ a wire electrostatic discharge machining method (described below in more detail).

However, the particular manufacturing process used for forming the groove is not essential to the energy delivery device as long as it provides the described transformation. Normally those who make or use the invention will select the manufacturing process based upon tooling and energy requirements, the expected application requirements of the final product, and the demands of the overall manufacturing process.

The cutting sharp tip 220 of the electrode can be formed as a cone (coaxial or noncoaxial with the principle axis of the elongated member; and cylindrically symmetric or asymmetric). Alternatively, the cutting sharp tip 220 of the electrode can be formed as a pyramid (e.g., a three sided pyramid, {a.k.a. a tri-bevel grind}). Conveniently, the tip 220 can be formed using an metal cutting method. These tip configurations can be provided on the distal end of the wire, or (with regard to embodiments described below) on the distal end of an attached tube, in the embodiments where a tube is connected to the distal end of the wire.

Referring now to FIG. 3, a wire based electrode 310 is depicted in the context of tissue penetration during a surgical procedure. The electrode 310 includes a superelastic wire 315 having a groove 320 in which is positioned a first thermocouple 330 (tip denoted $T_1$). The dashed line represents an isotherm. The electrode 310 is at least partially surrounded by an layer of insulation 340. The layer of insulation can advantageously include heat shrink tubing. A distal end of the layer of insulation 340 is inserted to a depth "d" beneath the surface of the tissue. The layer of insulation 340 substantially prevents heating of the tissue surrounding the layer of insulation 340. A second thermocouple 350 (tip denoted $T_2$) is positioned between the superelastic wire 315 and the layer of insulation 340. The second thermocouple 350 can be termed a safety device because it can signal an undesirable heating of tissue too near the surface. (It should be noted that the surface of a tissue is represented in FIG. 3 with a wavy line for improved clarity.)

FIG. 3 demonstrates substantially improved results that are unexpected. These results are represented by the dashed line that illustrates an isotherm. While not explicitly depicted in the two dimensional drawing, the isotherm is substantially cylindrically symmetric. Specifically, a substantially constant energy delivery rate results from the use of the electrode as $\theta$ is varied from 0 to $2\pi$ (R and r constant). This demonstrates the significant unexpected advantageous result that when a groove is cut in a wire based energy delivery device, the cylindrical symmetry of the energy field is not appreciably disrupted.

Figure 4A:
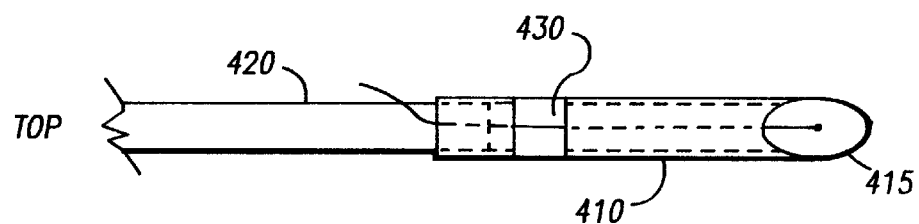
FIGS. 4A–4B illustrate schematic views of a wire based temperature sensing electrode, representing an embodiment of the invention.
Figure 4B:
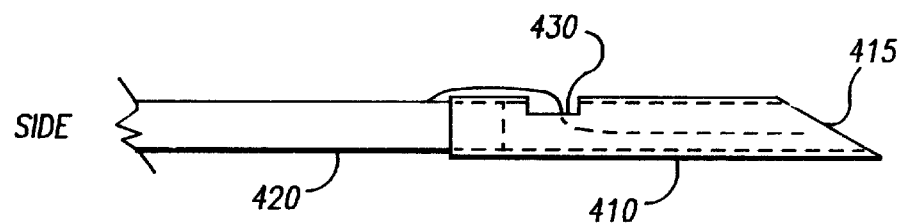

Referring now to FIGS. 4A–4B, an alternative embodiment of the invention is shown where a tube 410 is mechanically connected to a nickel-titanium wire 420. The tube 410 has a sharp tip 415. The tube 410 can be a hypotube. At least a portion of the tube 410 surrounds at least a portion of the wire 420. The tube 420 includes a temperature sensor lead slot 430. A thermocouple 440 is routed through the temperature sensor lead slot 430 and through at least a portion of the conduit defined by the tube 420. The thermocouple 440 is attached to the interior of the tube 410 with an adhesive.

The temperature sensor lead slot 430 in the tube 410 is preferably formed before the tube 410 is joined to the wire 420. Alternatively, the temperature sensor lead slot 430 can be formed after the tube 410 is joined to the wire 420. The temperature sensor lead slot 430 can be formed by machining, such as cutting or grinding, or by any other forming technique that yields an orifice suitable for routing the temperature sensor lead. (It should be noted that the surface of a tissue is represented in FIGS. 4A–4B with a wavy line for improved clarity.)

Referring now to FIG. 5, an insulating tubing 510 surrounds a wire 520 and a portion of a tube 530. A first thermocouple 540 is threaded beneath the tubing 510 and routed through a temperature sensor lead slot 550 that is formed in the tube 530. A tip $T_1$ of the first thermocouple 540 is located at a distal end 580 of the tube 530. A second thermocouple 560 is threaded beneath the tubing 510 along at least a portion of the wire 520 and at least a portion of the tube 530. A tip of the second thermocouple 560 is located at a distal end 570 of the tubing 510.

The temperature sensor lead slot 550 in the tube 530 can be processed by swaging or cold forging. Swaging can include squeezing one, or both, of the sides of the slot 550 that are parallel to a principle axis defined by the tube 530 so as to deform the side(s) to an appreciably different shape. For example, a force can be applied to the side(s) of the lead slot from the outside of the tube. Meanwhile, the remainder of the outer diameter of the tube can be rigidly supported. Optionally, a support pin can be inserted into the tube before the force is applied so as to better support the tube wall. The support pin can have one, or more, recess grooves that are opposite the direction in which the force is applied, thereby providing clearance and room for the deformed side(s) to travel in toward the principle axis of the tube. In this way, one or more internal ribs 590 can be formed within the tube to strengthen the tube against the weakness caused by the formation of the temperature sensor lead slot 550. The squeezing force should be applied to a relatively small area of the tube while the strained portion of the tube has freedom to flow without restraint.

Figure 6:
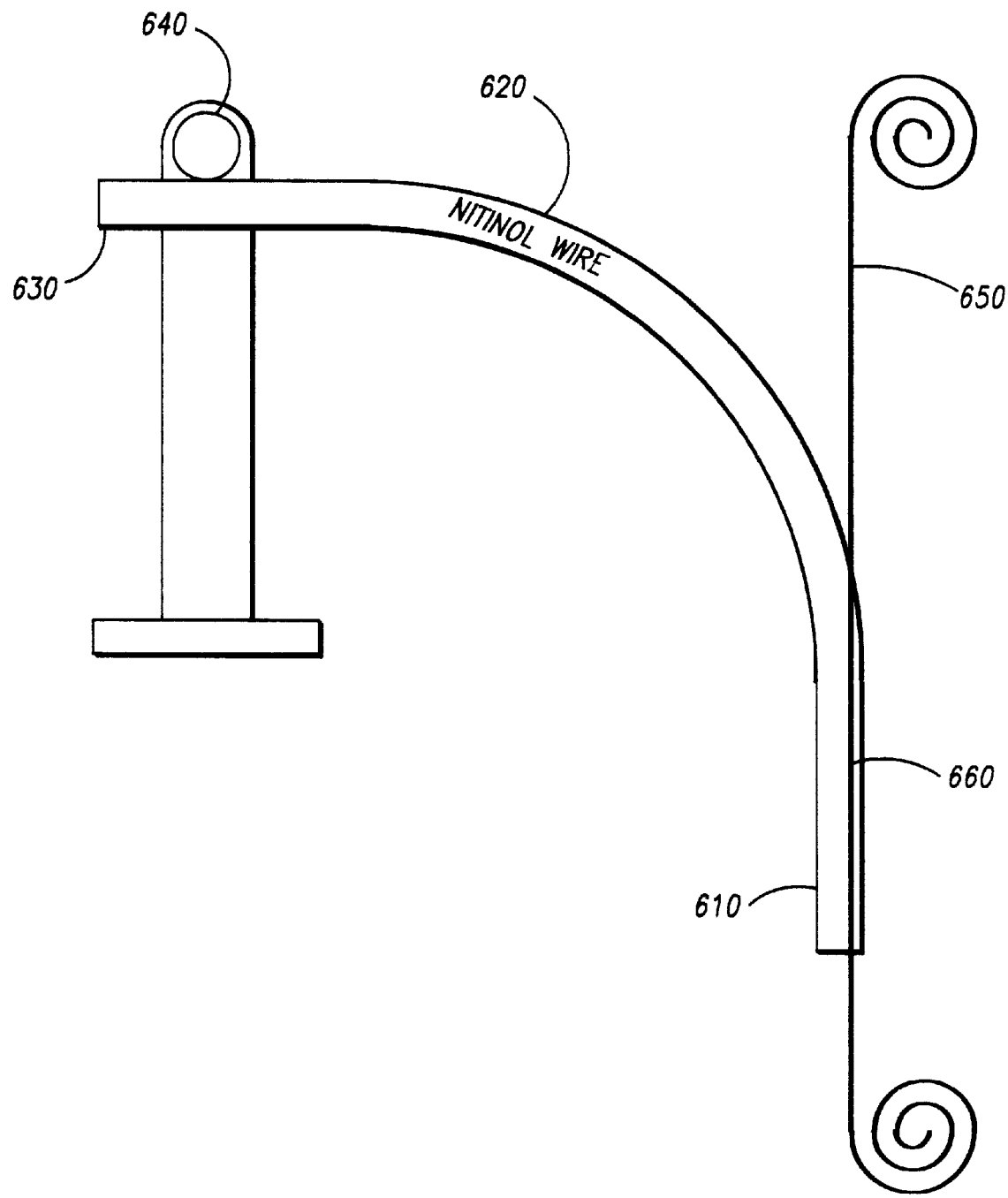
FIG. 6 illustrates a schematic view of tooling for wire electrostatic discharge machining a needle, representing an embodiment of the invention.

Referring to FIG. 6, a distal end 610 of a superelastic nickel titanium wire 620 is mounted so that a portion of a length defined by wire 620 held in a substantially rigid position. A proximal end 630 of the superelastic nickel titanium wire 620 is deflected by a pinion 640 so that the wire 620 is non-plastically deformed. The pinion 640 bends a proximal end of the wire 620 away from a principle axis defined by the distal end of the wire 620. In this way, an electrostatic discharge machining wire 650 can cut a groove 660. The groove 660 has a depth that decreases with increasing distance from the distal end 610. This can be termed a radial sweep defined by a depth that varies inversely as a function of distance from a distal end of the groove 660. It can be appreciated that the groove 660 can be cut more quickly in this way than with in the probe electrostatic discharge machining technique.

Since the wire 620 is composed of a superelastic material, the deflection may be relatively large without causing plastic deformation. However, this method is applicable to all elastic materials. Further, this method is applicable to all articles of manufacture and not just surgical instruments.

In those instances where the device is intended for surgical use, the particular material used for the elongated member (e.g., wire) should be suitable for insertion into tissue. In these cases, the wire of the invention should be made of a noncorrosive and tough material, such as, for example, stainless steel. Further, it is preferred that the material be a superelastic material. The use of a superelastic material is advantageous in that the wire can be temporarily formed into a curve of relatively small radius while retracted in a surgical instrument, without causing the wire to remain curved when extended from the instrument into the tissue. An example of a noncorrosive, tough, superelastic alloy is nickel titanium per MMS-117, which is readily commercially available from the Raychem Corporation of Menlo Park, Calif. (e.g., Ni=55.2%; Ti=44.5%; O=0.039%; Fe=0.034%; Cu=0.014%; C=0.010%; Al=0.007%; N=0.004%; Nb<0.001%; and H=0.0004%, by weight).

The particular material used for the adhesive should also be suitable for insertion into tissue. Conveniently, the adhesive of the invention can be made of any biocompatible high-tack material. For the manufacturing operation, it is moreover an advantage to employ an ultra-violet light curing epoxy material. The use of an ultra-violet light curing epoxy allows the components to be repositioned while in contact with one another. Further, the use of an ultra-violet light curing epoxy material of low viscosity permits the adhesive to be wicked into the groove, even after the temperature sensor leads have been positioned in the groove. An example of an ultraviolet light curing epoxy of low viscosity is 128-M-VLV, which is a urethane acrylate that is readily commercially available from the DYMAX Corporation of Torrington, Conn.

The particular material used for the temperature sensor leads should also be suitable for insertion into tissue, albeit less prone to direct contact with the tissue that the wire or adhesive materials discussed above. If, for example, the temperature sensor is a thermocouple, the sensor lead can include a first conductor of copper and a second conductor of constantan, thereby forming a type-T thermocouple. For the manufacturing operation, it is moreover an advantage to employ annealed sensor leads so that the leads are easier to route through the groove and undergo less work hardening. An example of such a sensor lead includes two parallel polyester enameled circular cross-section lengths of copper and constantan that are coated together with a layer of polyurethane. The outside diameter of the copper and/or constantan can be from approximately 0.0007 inch to approximately 0.0051 inch in outside diameter. Sensor leads in accordance with the foregoing example are readily commercially available from the California Fine Wire Company of Grover Beach, Calif.

However, the particular materials selected for the wire, epoxy, and sensor leads are not essential to the invention, as long as they provide the described functions. Normally, those who make or use the invention will select the best commercially available materials based upon the economics of cost and availability, the expected application requirements of the final product, and the demands of the overall manufacturing process.

While not being limited to any particular performance indicator, preferred embodiments of the invention can be identified one at a time by testing for the presence of low resistance to tissue insertion. The test for the presence of low resistance can be carried out without undue experimentation by the use of a simple and conventional force experiment by exerting a known force against the proximal end of an embodiment of the invention while the distal end penetrates a simulated tissue target. The magnitude of the scalar displacement can then be measured. Alternatively, embodiments can be evaluated by determining the variability of force needed to maintain a constant rate of travel through the tissue target.

EXAMPLES

Specific embodiments of the invention will now be further described by the following, nonlimiting examples which will serve to illustrate in some detail various features of significance. The examples are intended merely to facilitate an understanding of ways in which the invention may be practiced and to further enable those of skill in the art to practice the invention. Accordingly, the examples should not be construed as limiting the scope of the invention.

EXAMPLE 1

Referring to FIGS. 7A–7D, a wire based temperature sensing energy delivery device was formed by wire electrostatic discharge machining a 0.026 inch diameter, 7.62 inch long piece of nickel titanium round cross section wire. Referring to FIG. 7A, the resulting groove was approximately 0.500 inch long, approximately 0.012 inch deep and approximately 0.010 inch wide. The round edges at the bottom of the groove can be seen in FIG. 7A. The decreasing depth of the groove, due to the radial sweep, can be seen in FIG. 7B. A type T thermocouple was routed through the groove and fixed in place with 128-M-VLV ultraviolet curing epoxy.

EXAMPLE 2

Another wire based temperature sensing energy delivery device was formed by laser welding a piece of stainless steel tube to a piece stainless steel round cross section wire so that a portion of the tube surrounded a portion of the wire. The tube was previously formed by fabricating a sharp tip at a distal end of the tube and a temperature sensor lead slot near a proximal end of the tube. A type T thermocouple was routed through the temperature sensor lead slot and through the conduit defined by the tube. The tip of the thermocouple was fixed in place at the sharpened tip of the tube with 128-M-VLV ultraviolet curing epoxy.

Practical Applications of the Invention

A practical application of the invention that has value within the technological arts is treating the soft palette of the mouth. Further, the invention is useful in conjunction with treating the turbinates, or in conjunction with treating the tongue, or the like. There are virtually innumerable uses for the invention, all of which need not be detailed here.

Advantages of the Invention

A temperature sensing electrode, representing an embodiment of the invention, can be cost effective and advantageous for at least the following reasons. The invention utilizes a solid wire instead of a hollow tube, thereby significantly reducing the cost of the resulting product. The invention results in a stronger, more robust electrode because the solid wire is more resilient and less prone to damage.

All the disclosed embodiments of the invention described herein can be realized and practiced without undue experimentation. Although the best mode of carrying out the invention contemplated by the inventors is disclosed above, practice of the invention is not limited thereto. Accordingly, it will be appreciated by those skilled in the art that the invention may be practiced otherwise than as specifically described herein.

For example, the disclosed embodiments show a circular cross-section wire as the structure for performing the function of penetrating tissue, but the structure for penetrating tissue can be any other structure capable of performing the function of penetrating tissue, including, by way of example, a rod, a tube, a trocar, or even a scalpel blade, so long as the groove, or other conduit, for routing the sensor wires may be provided therein. Similarly, the structure for penetrating tissue can have any other cross-sectional shape, including, for instance, elliptical, rectilinear, or even parabolic.

Further, the rest of the individual components need not be formed in the disclosed shapes, or assembled in the disclosed configuration, but could be provided in virtually any shape, and assembled in virtually any configuration. Furthermore, the individual components need not be fabricated from the disclosed materials, but could be fabricated from virtually any suitable materials. Furthermore, although the temperature sensing electrode described herein is a physically separate module, it will be manifest that the temperature sensing electrode may be integrated into the apparatus with which it is associated. Furthermore, all the disclosed elements and features of each disclosed embodiment can be combined with, or substituted for, the disclosed elements and features of every other disclosed embodiment except where such elements or features are mutually exclusive. For instance, a hybrid embodiment of the invention could combine a wire having a groove with a tube having a temperature sensor lead slot.

It will be manifest that various additions, modifications and rearrangements of the features of the invention may be made without deviating from the spirit and scope of the underlying inventive concept. It is intended that the scope of the invention as defined by the appended claims and their equivalents cover all such additions, modifications, and rearrangements. The appended claims are not to be interpreted as including means-plus-function limitations, unless such a limitation is explicitly recited in a given claim using the phrase "means-for." Expedient embodiments of the invention are differentiated by the appended subclaims.

What is claimed is:

1. A method of making a temperature sensing energy delivery device, the device comprising:

an elongated member having a groove formed in at least portion thereof; and a first temperature sensor mechanically connected to said elongated member, said first temperature sensor including a first temperature sensor lead that is routed alone said groove;

the method comprising the steps of:

mounting a distal end of said elongated member so that a portion of a length defined by said elongated member is held substantially rigid;

bending a proximal end of said elongated member away from a principle axis defined by the distal end of said elongated member when said elongated member is not bent; and cutting said groove with an electrostatic discharge machining wire.

* * * * *